United States Patent [19]
Marquis et al.

[11] Patent Number: 5,962,699
[45] Date of Patent: Oct. 5, 1999

[54] PROCESS FOR DECOLORIZING ORGANIC CARBONATES

[75] Inventors: Edward T. Marquis, Austin; Robert E. Baldwin, Georgetown, both of Tex.

[73] Assignee: Huntsman Petrochemical Corporation, Austin, Tex.

[21] Appl. No.: 09/121,773

[22] Filed: Jul. 23, 1998

[51] Int. Cl.⁶ .......................... C07D 317/32; C07C 68/08
[52] U.S. Cl. .......................... 549/230; 549/228; 549/229; 558/270; 558/274; 558/276; 558/277
[58] Field of Search ............................. 549/230; 558/270, 558/274, 277

[56] References Cited

U.S. PATENT DOCUMENTS

| | | |
|---|---|---|
| 3,355,385 | 11/1967 | Mackley . |
| 3,843,578 | 10/1974 | Logemann et al. . |
| 3,925,008 | 12/1975 | Makino et al. . |
| 3,927,175 | 12/1975 | Garofano et al. ........................ 423/206 |
| 3,954,648 | 5/1976 | Belcak et al. . |
| 4,075,281 | 2/1978 | Port et al. ................................ 423/206 |
| 4,508,634 | 4/1985 | Elepano et al. . |
| 4,561,898 | 12/1985 | Fehr et al. . |
| 4,594,111 | 6/1986 | Coonan . |
| 4,927,556 | 5/1990 | Pokorny . |
| 4,956,115 | 9/1990 | Van De Mark . |
| 5,006,279 | 4/1991 | Grobbel et al. . |
| 5,085,795 | 2/1992 | Narayanan et al. . |
| 5,098,591 | 3/1992 | Stevens . |
| 5,098,594 | 3/1992 | Doscher . |
| 5,106,525 | 4/1992 | Sullivan . |
| 5,179,224 | 1/1993 | Takaki et al. . |
| 5,215,675 | 6/1993 | Wilkins et al. . |
| 5,331,103 | 7/1994 | Costantini et al. . |
| 5,334,331 | 8/1994 | Fusiak . |
| 5,414,153 | 5/1995 | Costantini et al. . |
| 5,425,893 | 6/1995 | Stevens . |
| 5,427,710 | 6/1995 | Stevens . |
| 5,489,696 | 2/1996 | Mendoza-Frohn et al. ............. 549/230 |
| 5,498,319 | 3/1996 | Ehlinger ............................... 558/274 X |
| 5,510,499 | 4/1996 | Mendoza-Frohn et al. ............. 549/229 |
| 5,585,526 | 12/1996 | Costantini et al. . |
| 5,597,788 | 1/1997 | Stevens . |
| 5,721,204 | 2/1998 | Maxwell et al. . |
| 5,728,666 | 3/1998 | Vitomir . |

FOREIGN PATENT DOCUMENTS

WO97/29158  8/1997  WIPO .

*Primary Examiner*—Michael G Ambrose
*Attorney, Agent, or Firm*—Jones, O'Keefe, Egan & Peterman

[57] ABSTRACT

A process for decolorizing organic carbonates, for example, cyclic alkylene carbonates, which involves contacting a discolored organic carbonate with hydrogen peroxide, is disclosed.

25 Claims, No Drawings

5,962,699

PROCESS FOR DECOLORIZING ORGANIC CARBONATES

BACKGROUND OF THE INVENTION

This invention pertains to a process for decolorizing organic carbonates, particularly, cyclic alkylene carbonates. In another aspect, this invention pertains to a decolorized organic carbonate composition.

As used hereinafter, the term "organic carbonate" includes cyclic alkylene carbonates and di(hydrocarbyl) carbonates, such as dialkyl carbonates, diaryl carbonates, and alkyl aryl carbonates.

Cyclic alkylene carbonates, such as propylene carbonate and butylene carbonate, have numerous uses including use in paint remover compositions and as developers and stripping solvents for photoresist materials. Dialkyl carbonates, such as dimethylcarbonate, are useful as solvents for cellulose derivatives and as starting materials for the preparation of diaryl carbonates, aliphatic and aromatic polycarbonates, pharmaceuticals, and plant protection agents. Diaryl carbonates, such as diphenyl carbonate, find utility in the preparation of thermoplastic polycarbonates.

Organic carbonates may exhibit a discoloration which may range from a light yellowish tinge to a rather intense yellow. Discoloration may arise from the formation of colored impurities or by-products during synthesis of the organic carbonate. The presence or absence of color in organic carbonates may also reflect the degree of refinement or purification to which the carbonate has been subjected. Alternatively, discoloration may arise from contaminants acquired during storage or handling of the carbonate. Discoloration in organic carbonates disadvantageously lowers product value. Reduction of the color may be desirable for esthetic reasons or for other reasons, such as when a high purity product is required for a given end use. High color in the carbonate can interfere with its use in coating applications, urethanes and epoxies where clear or light colors are required.

Distillation methods are known for removing impurities from organic carbonates. These methods are expensive and can only be used with carbonates which are capable of being distilled. Other purification methods, such as recrystallization and adsorption over a solid adsorbent, may be employed to remove color, but these methods are also expensive. In fact with carbonates, the color often cannot be removed by single distillation unless a very deep distillation cut is taken and the light material (10–40%) is discarded. This is very costly and wastefull. Further, it is often observed that early distillation cuts, though at first appearing clear in color, will turn yellow upon aging. In view of the above, it would be desirable to find a method for decolorizing organic carbonates which is inexpensive, easy to implement, and adaptable to a wide variety of organic carbonate products.

SUMMARY OF THE INVENTION

In a first aspect, this invention is a process for decolorizing organic carbonates. The process comprises contacting a discolored organic carbonate with hydrogen peroxide under reaction conditions sufficient to reduce the color.

The novel process of this invention is employed to reduce discoloration in organic carbonates. The reduction and, preferably, the removal of color advantageously improve the value of organic carbonates, both from the standpoint of esthetic appearance and from the standpoint of higher product purity. More advantageously, this invention is applicable to a wide variety of organic carbonates, including those which cannot be distilled. Even more advantageously, the peroxide, which is used to reduce the color, is needed only in small amounts and is not unduly harmful to the carbonate. Moreover, aqueous solutions of hydrogen peroxide can be used for this process even when there is only partial solubility of the carbonate in aqueous solution. Most advantageously, the process of this invention is inexpensive and easy to implement, as compared with distillation and other purification techniques. The aforementioned advantages make the process of this invention highly desirable for reducing discoloration found in organic carbonates.

In another aspect, this invention is a decolorized organic carbonate composition which comprises an organic carbonate and hydrogen peroxide wherein the hydrogen peroxide is present in a concentration ranging from greater than 0 to less than about 800 ppm, based on the weight of the carbonate.

In yet another aspect, this invention is a decolorized organic carbonate composition prepared by a process comprising contacting a discolored organic carbonate and hydrogen peroxide under reaction conditions sufficient to reduce the discoloration in the carbonate.

The composition of this invention comprises a decolorized organic carbonate which advantageously possesses higher commercial value than a discolored organic carbonate. The added value results from improved esthetic appearance and improved purity. Organic carbonates find utility as solvents, as starting materials for the preparation of polycarbonates, pharmaceuticals, and plant protection agents, and also find utility in the preparation of paint remover compositions, and developers and stripping agents for photoresist materials.

DETAILED DESCRIPTION OF THE INVENTION

The unique process of this invention involves reducing discoloration found in organic carbonates. The process comprises contacting a discolored organic carbonate with hydrogen peroxide under reaction conditions sufficient to reduce the color of the organic carbonate.

In a preferred embodiment of this invention, the process comprises reducing the color of a discolored cyclic alkylene carbonate. This preferred embodiment comprises contacting the discolored cyclic alkylene carbonate with hydrogen peroxide under reaction conditions sufficient to reduce the discoloration.

In another aspect, this invention is a decolorized organic carbonate composition. The composition comprises an organic carbonate and hydrogen peroxide wherein the peroxide is present in a concentration ranging from greater than 0 to less than about 800 ppm, based on the weight of the carbonate. In a preferred embodiment of this composition, the concentration of the peroxide ranges from greater than about 0 to less than about 300 ppm, based on the weight of the carbonate. More preferably, the decolorized organic carbonate is a cyclic alkylene carbonate.

In another aspect, this invention is a decolorized organic carbonate composition prepared by a process comprising contacting a discolored organic carbonate and hydrogen peroxide under reaction conditions sufficient to reduce the discoloration in the carbonate. Preferably, the organic carbonate is a cyclic alkylene carbonate.

Any discolored organic carbonate can be employed in the present invention. The test for discoloration may be made qualitatively by noting the visual appearance of the organic carbonate. Alternatively, the discoloration may be quantitatively measured using a standard platinum-cobalt color test. Typical discolored organic carbonates can measure from about 20 to about 40 on the platinum-cobalt color scale, and, in one embodiment, the discolored organic carbonate measures about 40. Suitable organic carbonates include cyclic alkylene carbonates and di(hydrocarbyl) carbonates, such as diallyl carbonates, diaryl carbonates, and alkyl aryl carbonates. Mixtures of these carbonates can also be employed.

The cyclic alkylene carbonate can contain from 3 to about 10 carbon atoms. Representative examples of cyclic alkylene carbonates include ethylene carbonate, propylene carbonate, and butylene carbonate.

The di(hydrocarbyl) carbonate can be represented by the formula:

wherein each R and $R^1$ can be the same or different, and may independently in each occurrence be selected from alkyl of from 1 to about 12 carbon atoms, and aryl of from about 6 to about 15 carbon atoms. Representative dialkyl carbonates include dimethyl carbonate, diethyl carbonate, di(isopropyl) carbonate, di(n-propyl) carbonate, di(n-butyl) carbonate, di(t-butyl) carbonate, and higher homologues of these. Representative diaryl carbonates include diphenyl carbonate and ditolyl carbonate. Representative alkyl aryl carbonates include methyl phenyl carbonate, ethyl phenyl carbonate, and methyl tolyl carbonate.

Substituted derivatives of the aforementioned organic carbonates may also be employed in the process of this invention. One or more substituents may be present on the alkyl or aryl moieties provided that the substituents are substantially inert with respect to the peroxide and process conditions. Non-limiting examples of suitable substituents include halo, alkoxy, hydroxy, and similar moieties. Representative examples of substituted organic carbonates include di(hydroxyethyl) carbonate, di(hydroxypropyl) carbonate, di(methoxyethyl) carbonate, and di(haloalkyl) carbonates.

Hydrogen peroxide is also required for the process of this invention. The hydrogen peroxide can be conveniently provided from commercial sources of hydrogen peroxide in water solutions of varying percentages. Hydrogen peroxide is commonly available as aqueous solutions at a concentration of from about 1 to about 80 weight percent. For example, industrial solutions are often 30 percent by weight hydrogen peroxide solutions. In the practice of this invention, use of aqueous hydrogen peroxide solutions ranging from about 20 to about 70 weight percent are preferred, with a concentration of about 30 to about 50 weight percent being more preferred.

It may be appreciated that highly concentrated hydrogen peroxide should be handled carefully and appropriately, since highly concentrated hydrogen peroxide is considered explosive.

Hydrogen peroxide is the preferred source of peroxide. With hydrogen peroxide there is no further requirement for separation or purification of the organic carbonate, as there might be with the use of organic peroxides.

The quantity of hydrogen peroxide which is used in the process of this invention can be any which allows for reduction of color in the organic carbonate. The quantity will depend upon the degree of discoloration, or from another perspective, upon the concentration of the contaminants causing the discoloration. Generally, about a minimal amount of hydrogen peroxide which is necessary to reduce the discoloration is used. One skilled in the art can easily determine what minimal amount of hydrogen peroxide substantially reduces discoloration of the sample. Typically, the quantity of hydrogen peroxide is greater than about 1 ppm and preferably, greater than about 10 ppm, based on the weight of the organic carbonate. Typically, the quantity of hydrogen peroxide is less than about 800 ppm and preferably, less than about 300 ppm, based on the weight of the organic carbonate.

The contacting of the discolored organic carbonate and hydrogen peroxide can be made using any contacting method which allows for reduction of the discoloration. Generally, the desired quantity of hydrogen peroxide is mixed with the carbonate in a liquid phase, preferably a neat carbonate liquid phase, using standard agitation methods appropriate for the sample size. The contacting temperature can vary depending upon the specific organic carbonate and the degree of color contamination. Typically, the contacting temperature is greater than or equal to about ambient temperature, taken as about 22° C., and preferably, greater than about 35° C. Typically, the contacting temperature is less than about 150° C., and preferably, less than about 100° C. Typically, the pressure ranges from about atmospheric to about 2000 psig (13.8 MPa), and preferably, from about atmospheric to about 10 psig.

When the organic carbonate cannot be readily liquefied, the process can be implemented by dissolving the organic carbonate in a suitable solvent and then treating the carbonate solution with the peroxide under the process conditions described hereinbefore. Any solvent which solubilizes the carbonate and is inert with respect to the peroxide is suitably employed. Representative solvents include low boiling aliphatic alcohols, and low boiling glycol ethers. Thereafter, the carbonate is separated from the solvent by methods known to those skilled in the art, such as distillation.

When a discolored organic carbonate is contacted with hydrogen peroxide under the process conditions described hereinbefore, the color of the organic carbonate is substantially reduced, and may be completely removed, as measured by the standard platinum-cobalt color test. Typical decolorized organic carbonates exhibit a platinum-cobalt color no greater than about 30, preferably, no greater than about 20, and more preferably, no greater than about 10.

The aforementioned method of decolorizing organic carbonates can be integrated into a larger synthetic process wherein a crude organic carbonate is first synthesized by methods known in the art and then decolorized by the method of this invention. Optionally, the crude organic carbonate may be purified or refined by distillation, recrystallization, or any other conventional separation or purification method either before or after the decolorizing step. Where the carbonate can be successfully decolorized by the addition of several amounts of aqueous hydrogen peroxide (for example 100–300 ppm of 30–50% $H_2O_2$), then the water can be left in the carbonate. Alternatively, if a low water, low glycol carbonate is desired, then distillation to remove the water and glycol will afford the decolorized of very pure carbonate.

The invention will be further clarified by consideration of the following examples, which are intended to be purely exemplary of the invention. Other embodiments of the invention will be apparent to those skilled in the art from consideration of this specification or practice of the invention as disclosed herein. Unless otherwise noted, parts per million (ppm) units are given on a weight basis.

EXAMPLE 1

A discolored ethylene carbonate sample from Huntsman's Conroe, Texas, plant was treated with aqueous hydrogen peroxide (35% $H_2O_2$ in $H_2O$) to a peroxide concentration of 300 ppm. The carbonate sample was maintained at 50° C. throughout the run. The platinum-cobalt color of the sample was measured at 2 and 4 hours and at 4 days with the results shown in Table 1.

TABLE 1

Platinum-Cobalt Color of Ethylene Carbonate

| Exp. | $H_2O_2$ (aq) (ppm) | 2 hours (50° C.) | 4 hours (50° C.) | 4 days (50° C.) |
|---|---|---|---|---|
| CE-1 | 0 | 40 | 40 | 40 |
| Ex. 1 | 300 | 10 | 10 | 5 |

Comparative Experiment 1

A sample of ethylene carbonate identical to that used in Example 1 was maintained at 50° C. for 4 days. The sample was not treated with hydrogen peroxide. The platinum-cobalt color of the untreated ethylene carbonate sample was measured at 2 and 4 hours and at 4 days with the results shown in Table 1. When Comparative Experiment 1 was compared with Example 1, it was seen that treatment of a discolored sample of ethylene carbonate with hydrogen peroxide effectively removed its platinum-cobalt color.

Experiment 2

A discolored 1,2-butylene carbonate sample was treated with aqueous hydrogen peroxide (35 weight percent solution) in varying concentrations as shown in Table 2. The platinum-cobalt color of the sample was measured at the start of the experiment and at 15 days, as shown in Table 2. Temperature was maintained at 22–25° C. throughout the run.

TABLE 2

Platinum-Cobalt Color of 1,2-Butylene Carbonate

| Exp. | $H_2O_2$ (aq) (ppm) | t = 0 (22–25° C.) | t = 15 d (22–25° C.) |
|---|---|---|---|
| CE-2 | 0 | 40 | 40 |
| Ex. 2 | 3 | 40 | 20 |
| Ex. 2 | 30 | 40 | 20 |
| Ex. 2 | 300 | 40 | 20 |

Comparative Experiment 2

A sample of 1,2-butylene carbonate identical to that used in Example 2 was maintained at 22–25° C. for 15 days. The sample was not treated with hydrogen peroxide. The platinum-cobalt color of the untreated butylene carbonate sample was measured at the start of the experiment and at 15 days with the results shown in Table 2. The color of the untreated carbonate sample was found to be stable over the length of the experiment. When Comparative Experiment 2 was compared with Example 2, it was seen that treatment of the discolored butylene carbonate with hydrogen peroxide at concentrations ranging from 3 ppm to 300 ppm reduced the platinum-cobalt color of the carbonate by 50 percent.

Experiment 3

A discolored ethylene carbonate sample from Huntsman's Conroe, Texas, plant was treated with aqueous hydrogen peroxide (35 weight percent solution) in varying concentrations as shown in Table 3. The carbonate sample was maintained at 50° C. throughout the run. The platinum-cobalt color of the sample was measured at 1, 2, and 3 weeks with the results shown in Table 3.

TABLE 3

Platinum-Cobalt Color of Ethylene Carbonate

| Exp. | $H_2O_2$ (ppm) | 1 wk (50° C.) | 2 wk (50° C.) | 3 wk (50° C.) |
|---|---|---|---|---|
| CE-1 | 0 | 40 | 40 | 40 |
| Ex. 3 | 300 | 10 | 10 | 10 |
| Ex. 3 | 200 | 10 | 10 | 10 |
| Ex. 3 | 100 | 20 | 15 | 15 |

Comparative Experiment 3 (CE-3)

A sample of ethylene carbonate identical to that used in Example 3 was maintained at 50° C. for 4 weeks. The sample was not treated with hydrogen peroxide. The platinum-cobalt color of the untreated ethylene carbonate sample was measured at 1, 2, and 3 weeks with the results shown in Table 3. The color was found to be stable over the three weeks and also remained unchanged during the fourth week. When Comparative Experiment 3 was compared with Example 3, it was seen that treatment of the discolored ethylene carbonate with hydrogen peroxide substantially reduced its platinum-cobalt color.

What is claimed is:

1. A process for decolorizing an organic carbonate comprising contacting a discolored organic carbonate with hydrogen peroxide under reaction conditions sufficient to reduce the color of the organic carbonate.

2. The process of claim 1 wherein the organic carbonate is a cyclic alkylene carbonate.

3. The process of claim 2 wherein the cyclic alkylene carbonate comprises from 3 to about 10 carbon atoms.

4. The process of claim 3 wherein the cyclic alkylene carbonate is ethylene carbonate, propylene carbonate, or butylene carbonate.

5. The process of claim 1 wherein the organic carbonate is a di(hydrocarbyl) carbonate selected from dialkyl carbonates, diaryl carbonates, and alkyl aryl carbonates.

6. The process of claim 5 wherein the di(hydrocarbyl) carbonate is represented by the formula:

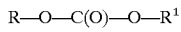

$$R-O-C(O)-O-R^1$$

wherein R and $R^1$ are the same or different, and are each independently selected from $C_{1-2}$ alkyl and $C_{6-15}$ aryl groups.

7. The process of claim 6 wherein the di(hydrocarbyl) carbonate is a dialkyl carbonate selected from the group consisting of dimethyl carbonate, diethyl carbonate, di(n-propyl) carbonate, di(isopropyl) carbonate, di(n-butyl) carbonate, and di(t-butyl) carbonate.

8. The process of claim 6 wherein the di(hydrocarbyl) carbonate is a diaryl carbonate selected from the group consisting of diphenyl carbonate and ditolyl carbonate.

9. The process of claim 1 wherein hydrogen peroxide is provided as aqueous hydrogen peroxide.

10. The process of claim 9 wherein the concentration of aqueous hydrogen peroxide used to treat the carbonate ranges from about 1 to about 80 weight percent.

11. The process of claim 10 wherein the concentration of aqueous hydrogen peroxide used to treat the organic carbonate ranges from about 30 to about 50 weight percent.

12. The process of claim 1 wherein a quantity of peroxide is employed which is greater than about 1 ppm and less than about 800 ppm, based on the weight of the organic carbonate.

13. The process of claim 1 wherein a quantity of peroxide is employed which is greater than about 10 ppm and less than about 300 ppm, based on the weight of the organic carbonate.

14. The process of claim 1 wherein the process is conducted at a temperature ranging from greater than about 22° C. to less than about 150° C.

15. The process of claim 1 wherein the process is conducted at a pressure ranging from about atmospheric to about 2000 psig (13.8 MPa).

16. The process of claim 1 wherein the organic carbonate exhibits after treatment with peroxide a platinum-cobalt color no greater than about 20.

17. The process of claim 1 wherein the organic carbonate exhibits after treatment with peroxide a platinum-cobalt color no greater than about 10.

18. A method of preparing a decolorized organic carbonate composition comprising (a) synthesizing a crude organic carbonate, (b) subjecting the crude organic carbonate to a decolorizing step by contacting the crude organic carbonate with hydrogen peroxide under reaction conditions sufficient to reduce color in the organic carbonate, and (c) optionally, either before or after the decolorizing step, subjecting the organic carbonate to additional purification or separation.

19. The process of claim 18 wherein the organic carbonate is ethylene carbonate, propylene carbonate, or butylene carbonate.

20. The process of claim 18, wherein the organic carbonate is propylene carbonate.

21. The process of claim 18, wherein the hydrogen peroxide is aqueous hydrogen peroxide.

22. The process of claim 18, wherein the hydrogen peroxide is aqueous hydrogen peroxide having a hydrogen peroxide concentration of from about 30 to about 50 weight percent.

23. The process of claim 18, wherein the hydrogen peroxide is present in an amount of from about 1 ppm to about 800 ppm, based on the weight of the organic carbonate.

24. The process of claim 18, wherein the hydrogen peroxide is present in an amount of from about 10 ppm to about 300 ppm based on the weight of the carbonate.

25. The process of claim 18, wherein the organic carbonate is subjected to additional purification after decolorization, wherein the purification is by distillation.

* * * * *